(12) United States Patent
Yi et al.

(10) Patent No.: US 12,217,869 B2
(45) Date of Patent: Feb. 4, 2025

(54) IMAGE DIAGNOSIS APPARATUS USING DEEP LEARNING MODEL AND METHOD THEREFOR

(71) Applicants: KOREA ADVANCED INSTITUTE OF SCIENCE AND TECHNOLOGY, Daejeon (KR); SEEGENE MEDICAL FOUNDATION, Seoul (KR)

(72) Inventors: Mun Yong Yi, Daejeon (KR); Young Jin Park, Daejeon (KR); Jong Kee Chun, Seoul (KR); Young Sin Ko, Seoul (KR)

(73) Assignees: KOREA ADVANCED INSTITUTE OF SCIENCE AND TECHNOLOGY, Daejeon (KR); SEEGENE MEDICAL FOUNDATION, Seoul (KR)

( * ) Notice: Subject to any disclaimer, the term of this patent is extended or adjusted under 35 U.S.C. 154(b) by 353 days.

(21) Appl. No.: 17/624,621

(22) PCT Filed: Jun. 30, 2020

(86) PCT No.: PCT/KR2020/008502
§ 371 (c)(1),
(2) Date: Jan. 4, 2022

(87) PCT Pub. No.: WO2021/006522
PCT Pub. Date: Jan. 14, 2021

(65) Prior Publication Data
US 2022/0270756 A1    Aug. 25, 2022

(30) Foreign Application Priority Data
Jul. 5, 2019 (KR) .................. 10-2019-0081416

(51) Int. Cl.
*G16H 50/20* (2018.01)
*G06N 3/045* (2023.01)
*G16H 30/20* (2018.01)

(52) U.S. Cl.
CPC ............. *G16H 50/20* (2018.01); *G06N 3/045* (2023.01); *G16H 30/20* (2018.01)

(58) Field of Classification Search
CPC ........ G16H 50/20; G16H 30/20; G16H 50/70; G16H 30/40; G06N 3/045; G06F 18/2415;
(Continued)

(56) References Cited

U.S. PATENT DOCUMENTS 4,965,725 A    10/1990    Rutenberg
8,712,142 B2 *    4/2014    Rajpoot ................ G06T 7/0012
                                                                435/6.14
(Continued)

FOREIGN PATENT DOCUMENTS

EP    0336608 A2    10/1989
JP    2018045516 A    3/2018
(Continued)

OTHER PUBLICATIONS

International Search Report (in English and Korean) and Written Opinion (in Korean) issued in PCT/KR2020/008502, mailed Oct. 8, 2020; ISA/KR.
(Continued)

*Primary Examiner* — Neil R McLean
(74) *Attorney, Agent, or Firm* — Harness, Dickey & Pierce, P.L.C.

(57) ABSTRACT

The present specification discloses an image diagnosis apparatus using a deep learning model and a method therefor, wherein tissue included in an input medical image is classified as being one of normal and abnormal for a disease by
(Continued)

using the trained deep learning model using a weighted loss function in which different weights are assigned to a probability distribution of determining that a picture extracted from the input medical image is abnormal even though it is normal and a probability distribution of determining that the picture is normal even though it is abnormal.

20 Claims, 10 Drawing Sheets

(58) Field of Classification Search
CPC .............. G06V 10/82; G06V 2201/03; G06T 2207/20081; G06T 2207/20084; G06T 2207/30004; G06T 7/0012; A61B 5/0033; A61B 5/7275
USPC ........................................................ 382/128
See application file for complete search history.

(56) References Cited

U.S. PATENT DOCUMENTS

| | | | |
|---|---|---|---|
| 10,102,444 B2 | 10/2018 | Kim et al. | |
| 11,301,991 B2 * | 4/2022 | Reicher | G16H 10/20 |
| 11,562,820 B2 | 1/2023 | Papagiannakis et al. | |
| 2018/0060722 A1 | 3/2018 | Hwang et al. | |
| 2019/0130279 A1 * | 5/2019 | Beggel | G06V 10/82 |

FOREIGN PATENT DOCUMENTS

| | | |
|---|---|---|
| KR | 1020180025093 A | 3/2018 |
| KR | 1020180040287 A | 4/2018 |
| KR | 1020180057420 A | 5/2018 |
| RU | 2096827 C1 | 11/1997 |
| RU | 2765619 C1 | 2/2022 |
| WO | 2019075410 A1 | 4/2019 |
| WO | 2019079166 A1 | 4/2019 |

OTHER PUBLICATIONS

Godkhindi Akshay M, et al: "Automated detection of polyps in CT colonography images using deep learning algorithms in colon cancer diagnosis", International Conference on Energy, Communication, Data Analytics and Soft Computing (ICECDS-2017) (7 pages).

Chen Tianhua, et al: "Reliability-guided fuzzy classifier ensemble", IEEE (2017) (6 pages).

* cited by examiner

IMAGE DIAGNOSIS APPARATUS USING DEEP LEARNING MODEL AND METHOD THEREFOR

CROSS-REFERENCE TO RELATED APPLICATIONS

This application is a U.S. National Phase Application under 35 U.S.C. 371 of International Application No. PCT/KR2020/008502, filed Jun. 30, 2020, which claims the benefit of Korean Patent Application No. 10-2019-0081416, filed Jul. 5, 2019. The entire disclosures of the above applications are incorporated herein by reference.

TECHNICAL FIELD

The present disclosure relates to an image diagnosis apparatus using a deep learning model for diagnosing a disease of tissue included in an image and a method therefor.

BACKGROUND ART

In general, an image diagnosis apparatus is a technology for automatically determining the presence or absence of a disease from a medical image using a computer so as to assist a doctor in diagnosis.

A general image diagnosis apparatus focuses on increasing the accuracy of detection of the presence or absence of a disease by applying a deep learning model, but does not actually assist a doctor in diagnosis even if the accuracy of detection of the presence or absence of a disease is increased.

DISCLOSURE

Technical Problem

The present embodiments may provide an image diagnosis apparatus using a deep learning model for increasing specificity of image diagnosis or increasing sensitivity of image diagnosis, and a method therefor.

In addition, the present embodiments may provide an image diagnosis apparatus using a deep learning model for minimizing an image diagnosis error which may result in fatal complications for a patient through an optimal treatment time of a disease being delayed or missed, and a method therefor.

Technical Solution

According to an aspect, the present embodiments may provide an image diagnosis apparatus using a deep learning model and a method therefor, wherein tissue included in an input medical image is classified as being one of normal and abnormal in terms of the presence of disease using a trained deep learning model using a weighted loss function in which different weights are assigned to a probability distribution of determining that a feature extracted from the input medical image is abnormal even though the feature is normal and a probability distribution of determining that the feature is normal even though the feature is abnormal.

According to another aspect, the present embodiments may provide an image diagnosis apparatus using a deep learning model, including: an image input part receiving a medical image including tissue of a human body; a classifier classifying the tissue included in the medical image as being one of normal and abnormal in terms of the presence of disease using a trained deep learning model using a weighted loss function in which different weights are assigned to a probability distribution of determining that a feature extracted from the input medical image is abnormal even though the feature is normal and a probability distribution of determining that the feature is normal even though the feature is abnormal; and a result output part outputting a result of classification by the classifier.

According to still another aspect, the present embodiments may provide an image diagnosis method using a deep learning model, including: an image input operation of receiving a medical image including tissue of a human body; a classification operation of classifying the tissue included in the input medical image as being one of normal and abnormal in terms of the presence of disease using a trained deep learning model using a weighted loss function in which different weights are assigned to a probability distribution of determining that a feature extracted from the input medical image is abnormal even though the feature is normal and a probability distribution of determining that the feature is normal even though the feature is abnormal; and a result output operation of outputting a result of classification in the classification operation.

Advantageous Effects

An image diagnosis apparatus using a deep learning model and a method therefor, according to the present embodiments, may increase specificity of image diagnosis or increase sensitivity of image diagnosis.

In addition, an image diagnosis apparatus using a deep learning model and a method therefor, according to the present embodiments, may minimize an image diagnosis error which may result in fatal complications for a patient through an optimal treatment time of a disease being delayed or missed.

MODE FOR INVENTION

Figure 1:
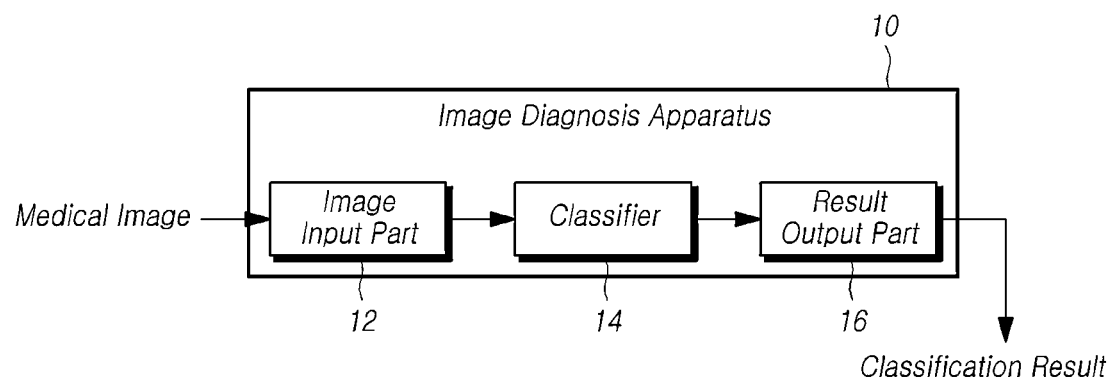
FIG. 1 is a conceptual diagram of an image diagnosis apparatus using a deep learning model, according to an embodiment of the present disclosure.

Hereinafter, some embodiments of the present disclosure will be described in detail with reference to the exemplary drawings. In assigning reference numerals to components of each drawing, the same components may have the same reference numerals as much as possible even though the components are illustrated in different drawings. In addition, in describing the present embodiments, if the detailed description of the relevant known functions or configurations is determined to unnecessarily obscure the gist of the present disclosure, the detailed description thereof may be omitted. When the terms "including", "having", "consisting of", and the like are used, other components may be added unless "only" is used. When a component is expressed in the singular, it may include a case in which the plural is included unless otherwise explicitly stated.

Terms, such as "first", "second", "A", "B", "(A)", or "(B)" may be used herein to describe elements of the present disclosure. Each of these terms is not used to define the essence, order, sequence, or number of elements etc., but is used merely to distinguish the corresponding element from other elements.

In the description of the positional relationship of the components, if it is described that two or more components are "connected", "coupled", or "linked", etc., two or more components may be directly "connected", "coupled", or "linked", but it will be understood that other components other than the two or more components may be further "interposed" to be "connected", "coupled", or "linked". The other components may be included in at least one of two or more components that are "connected", "coupled", or "linked" to each other.

In the description of the temporal flow relationship related to the components, the operating method, or the manufacturing method, for example, when the temporal precedence or flow precedence is described using "after", "subsequent", "thereafter", "before", etc., it may include cases that are not continuous unless "just" or "directly" is used.

On the other hand, when numerical values for components or their corresponding information (e.g., levels, etc.) are mentioned, even if there is no separate explicit description, the numerical values or their corresponding information may be interpreted as including an error range that may occur due to various factors (e.g., process factors, internal or external impact, noise, etc.).

Throughout the detailed description and the claims of the present disclosure, 'learning' is a term referring to performing machine learning through computing according to a procedure. Thus, a person having ordinary skill in the art may understand that it is not intended to refer to a mental action such as human educational activity.

Embodiments of the present disclosure will be described in detail with reference to the drawings.

Figure 2:
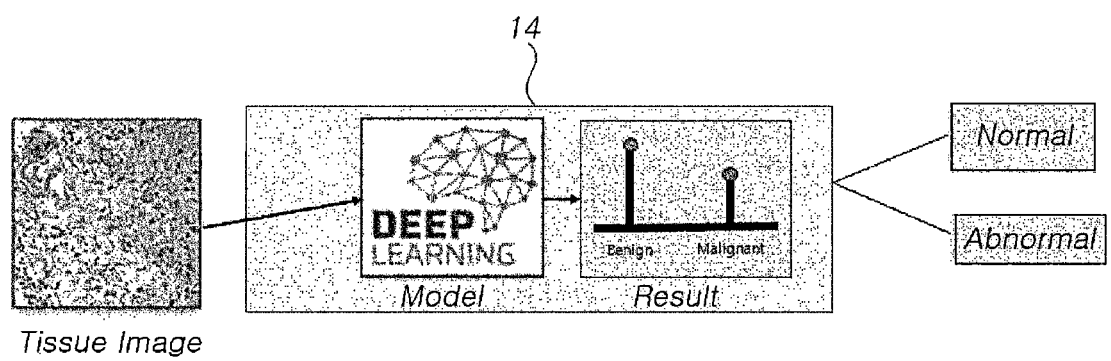
FIG. 2 is a conceptual diagram of a classifier of FIG. 1.

FIG. 1 is a conceptual diagram of an image diagnosis apparatus using a deep learning model, according to an embodiment of the present disclosure. FIG. 2 is a conceptual diagram of a classifier of FIG. 1.

Referring to FIG. 1, an image diagnosis apparatus 10 using a deep learning model, according to an embodiment of the present disclosure, includes an image input part 12 receiving an image, a classifier 14 classifying the image with a trained deep learning model using a weighted loss function to which different weights are assigned, and a result output part 16 outputting a result of classification by classifier 14.

The image input part 12 may receive a medical image including tissue of a living organism, for example, tissue of a human body. For example, the image input part 12 may receive a medical image from a medical imaging system that captures medical images of tissue of a human body and stores the captured images.

The medical image may be the tissue of the human body, for example, liver, stomach, heart, small intestine, large intestine, etc. In addition, a disease may be cancer, inflammation, a rupture, etc. In the present specification, a case in which the medical image is an image captured from the large intestine of the human body and the disease is colon cancer will be described as an example, but the present disclosure is not limited thereto.

In the present specification, the deep learning model may be in the form in which artificial neural networks are stacked in multilayered layers. That is, the deep learning model is configured to automatically learn features of images by learning a large amount of data from a deep neural network including a multilayered network and learn a network by minimizing an objective function, that is, an error of prediction accuracy.

In the present specification, the deep learning model may use, for example, a Convolutional Neural Network (CNN), a Deep Hierachical Network (DHN), a Convolutional Deep Belief Network (CDBN), a Deconvolutional Deep Network (DDN), etc., but may use various current or future deep learning models. In the present specification, an example of using a CNN-based deep learning model will be described, but the present disclosure is not limited thereto, and various current or future deep learning models may be used.

A framework creates functions commonly used to develop deep learning models in advance and provides the functions in library form. The frame enables system software or a hardware platform below an operating system level to be used efficiently. In the present embodiment, the deep learning framework may develop a deep learning model using any framework which is currently available to the public or which will be released in the future.

In general, in medical science, particularly in laboratory medicine or preventive medicine, concepts such as accuracy, sensitivity, and specificity are important as measures of image diagnosis.

That is, as shown in Table 1, a case in which a test result is positive, and there is a disease present is referred to as a true positive, while a case in which there is actually no disease present is referred to as a false positive. A case in which a test result is negative, but there is actually a disease present is referred to as a false negative, and a case in which there is actually no disease present is referred to as a true negative. The false positive and the false negative are diagnostic result errors. The former is referred to as a type I error and the latter is referred to as a type II error.

TABLE 1

|  | With disease present (patient) | Without disease present (normal person) |
| --- | --- | --- |
| Test result: positive | True positive | False positive |
| Test result: negative | False negative | True negative |

In this case, the accuracy, the specificity, and the sensitivity are represented by Equation 1 to 3 below.

$$\text{Accuracy} = \frac{\text{True positive} + \text{True negative}}{\text{True positive} + \text{True negative} + \text{False positive} + \text{False negative}} \quad \text{Equation 1}$$

$$\text{Specificity} = \frac{\text{True negative}}{\text{True negative} + \text{False positive}} \quad \text{Equation 2}$$

$$\text{Sensitivity} = \frac{\text{True positive}}{\text{True positive} + \text{False negative}} \quad \text{Equation 3}$$

In general, the deep learning model may be used to classify whether or not there is a disease present in a corresponding tissue for image diagnosis. A general deep learning model focuses only on increasing the accuracy of image diagnosis when classifying whether or not there is a disease present in a corresponding tissue for image diagnosis.

Increasing the accuracy of image diagnosis is minimizing both the type I error and the type II error described above. Minimizing the type I error is increasing specificity, and minimizing the type II error is increasing sensitivity.

As described above, since the general deep learning model focuses only on increasing the accuracy of image diagnosis, the general deep learning model could not focus on increasing the sensitivity of image diagnosis or increasing the specificity of image diagnosis.

The classifier 14 performs image diagnosis using a weighted loss function-based deep learning model focusing on increasing the sensitivity of image diagnosis or increasing the specificity of image diagnosis.

In particular, for patient treatment in an image diagnosis test, it may be much more important to minimize the false-negative type II error than the false-positive type I error. This is because, in an image diagnosis test, an image diagnosis test may show that there is no disease, and a patient with an actual disease may delay or miss the optimal treatment time for the disease, which may result in fatal complications for the patient.

For example, the classifier 14 may perform image diagnosis using the weighted loss function-based deep learning model focusing on increasing the sensitivity of image diagnosis.

Referring to FIG. 2, the classifier 14 classifies tissue included in an input medical image as being one of normal and abnormal in terms of the presence of disease using a trained deep learning model using weighted loss functions to which different weights are assigned.

In general, the deep learning model aims to make a probabilistic prediction about an input through an artificial neural network-type model and to adjust model parameters as closely as possible to the ground-truth probability of the prediction. For example, if the ground-truth probability is y=(1.0, 0.0) and the prediction of the deep learning model is Y=(0.4, 0.6), the model parameter has to be adjusted so that Y has a value that is 'closer' to y. A measure of 'close', in other words, a method of determining whether there is a difference is required. In the field of deep learning, a loss function is defined for this purpose. For example, in the field of deep learning, various loss functions, as shown in Equation 4, may be used.

Loss function=$L$(abnormal|normal)+$L$(normal|abnormal)      Equation 4

In Equation 4, $L$(abnormal|normal) is a probability distribution of determining that a feature is abnormal even though the feature is normal. $L$(normal|abnormal) is a probability distribution of determining feature is normal even though the feature is abnormal.

As described above, the classifier 14 performs image diagnosis using a weighted loss function-based deep learning model focusing on increasing the specificity of image diagnosis or increasing the accuracy of image diagnosis.

That is, the loss function used by the classifier 14 may be a weighted loss function in which different weights are assigned to the probability distribution ($L$(abnormal|normal)) of determining that a feature is abnormal even though the feature is normal and the probability distribution ($L$(normal|abnormal)) of determining that a feature is normal even though the feature is abnormal.

In other words, the weighted loss function used by the classifier 14 may be a weighted loss function in which different weights $W_1$ and $W_2$ ($W_1 \neq W_2$) are assigned to the probability distribution of determining that the feature extracted from the input medical image is abnormal even though the feature is normal and the probability distribution of determining that the feature is normal even though the feature is abnormal.

Weighted loss function=$W_1$*$L$(abnormal|normal)+
$W_2$*$L$(normal|abnormal)      Equation 5

In Equation 5, $W_1$ is a first weight assigned to the probability distribution of determining that a feature is abnormal even though the feature is normal. $W_2$ is a second weight assigned to the probability distribution of determining that the feature is normal even though a feature is abnormal. $W_1$ and $W_2$ are real numbers greater than 0.

In particular, cross entropy as shown in Equation 6 below is generally used in the classification problems in the field of deep learning.

$$\text{cross entropy} = -\frac{1}{N}\sum_{i=1}^{N} y_i \log(\hat{y}) \quad \text{Equation 6}$$

In Equation 6, $y_i = \{0 \text{ (normal)}, 1 \text{ (abnormal)}\}$, and $\hat{y}$ is an estimate estimated by each model and is a real number of 0 to 1.

If the cross entropy in Equation 6 is applied to the weighted loss function in Equation 5, it is summarized as in Equation 7.

$$\text{Weighted loss function} = -\frac{1}{N}\sum_{i=1}^{N}(W_1 y_i \log(\hat{y}_i) + W_2(1-y_i)\log(1-\hat{y}_i)) \quad \text{Equation 7}$$

In Equation 7, $y_i = \{0 \text{ (normal)}, 1 \text{ (abnormal)}\}$, and $\hat{y}_i$ is an estimate estimated by each model and is a real number of 0 to 1.

As described above, for patient treatment in a diagnosis test, it may be much more important to minimize the false-negative type II error than the false-positive type I error.

In order to focus on increasing the accuracy of image diagnosis, in the weighted loss function, the second weight $W_2$ assigned to the probability distribution of determining that a feature is normal even though the feature is abnormal may be greater than the first weight $W_1$ assigned to the probability distribution of determining that a feature is abnormal even though the feature is normal ($W_1 < W_2$).

For ease of determination, the first weight $W_1$ and the second weight $W_2$ may be natural numbers. For example, the first weight $W_1$ may be 1, and the second weight $W_2$ may be a natural number greater than 1.

Figure 3:
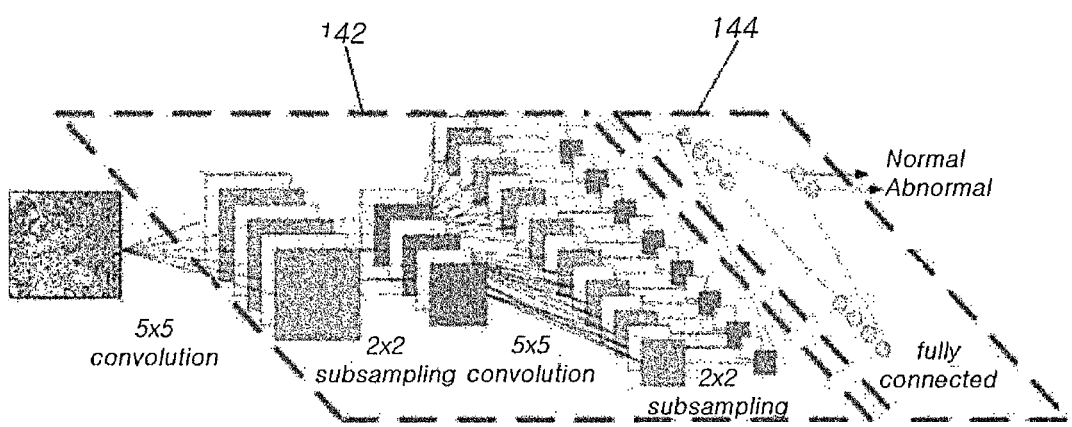
FIG. 3 is a configuration diagram of a deep learning model used by the classifier of FIG. 1.

FIG. 3 is a configuration diagram of the deep learning model used by the classifier of FIG. 1.

Referring to FIG. 3, the deep learning model used by the classifier 14 includes a feature extraction part 142 extracting a feature of a medical image by performing convolution and subsampling on the input medical image, and a classification part 144 classifying the input medical image using the weighted loss function with respect to the extracted feature.

The convolution creates a feature map using a plurality of filters for each region of the medical image in a convolution layer. The subsampling or pooling reduces the size of the feature map in a subsampling layer to extract a feature of the medical image that is invariant to a change in position or rotation.

The feature extraction part 142 may repeat the convolution and/or the subsampling to extract features of various levels from low-level features such as points, lines, or planes to complex and meaningful high-level features in the medical image.

The classification part 144 uses the feature ultimately extracted by the feature extraction part 142 as an input value for the weighted loss function of Equation 7.

The deep learning model, for example, the CNN-based deep learning model, aims to optimally learn parameters present in each individual layer in the feature extraction part 142 and the classification part 144. In the deep learning model, the order of pieces of data determines a value of an initial parameter.

The deep learning model may apply random sampling (data order random) and a regulation technique. The random sampling means that the order of pieces of training data learned in a training data set is different.

The regulation technique is a technique that reduces over-fitting in which a deep learning model over-trained on training data including even noise is less accurate in testing or diagnosis. The regulation technique may be, for example, a dropout technique or a drop connected technique.

The dropout technique is a method of probabilistically setting a parameter value as 0 or a specific node and performing learning. The drop connected technique is a method of dropping and learning connections between nodes. The dropout technique will be described below as an example of the regulation technique, but any current or future technique or algorithm that reduces over-fitting may be used.

Figure 4A:
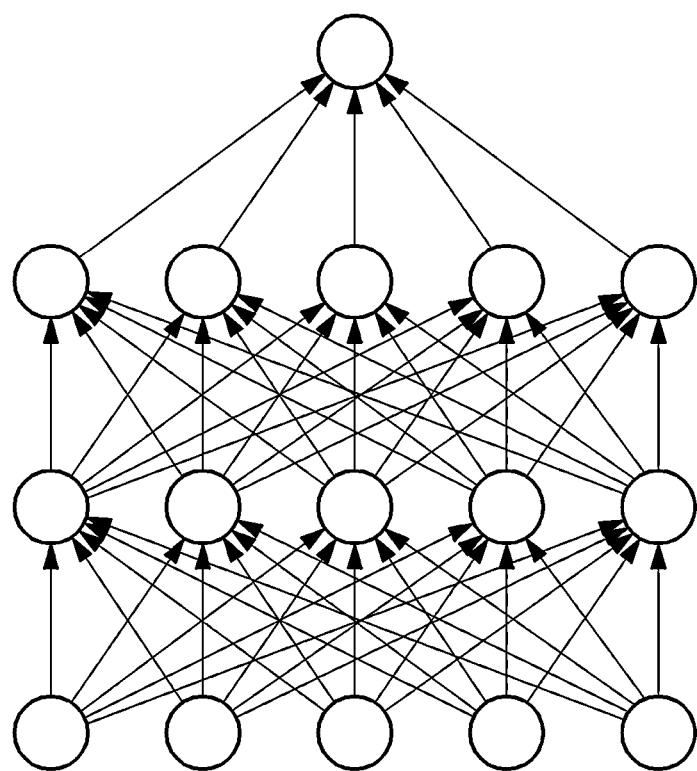
FIGS. 4A and 4B illustrate connection states of all nodes if the deep learning model used by the classifier of FIG. 1 applies a dropout technique and if the deep learning model used by the classifier of FIG. 1 does not apply a dropout technique.
Figure 4B:
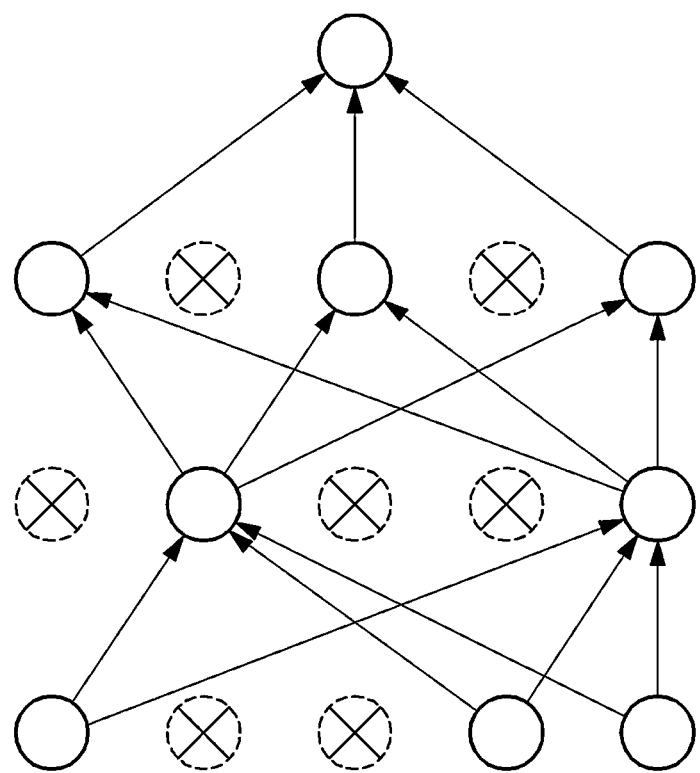

FIGS. 4A and 4B illustrate connection states of all nodes if the deep learning model used by the classifier of FIG. 1 applies the dropout technique and if the deep learning model used by the classifier of FIG. 1 does not apply the dropout technique. In FIG. 4B, X refers to a node removed from each layer.

Referring to FIG. 4B, the deep learning model used by the classifier 14 may apply a dropout technique that learns training data by removing a node present in each layer with a specific probability p and, when the learning is completed and the actual image is classified, considers all nodes as they are and multiplies the probability p by the weight of each node.

The dropout technique may interfere with the learning by randomly removing nodes present in each layer when the deep learning model is trained, thereby preventing over-fitting in which the learning is biased to the training data.

Figure 5:
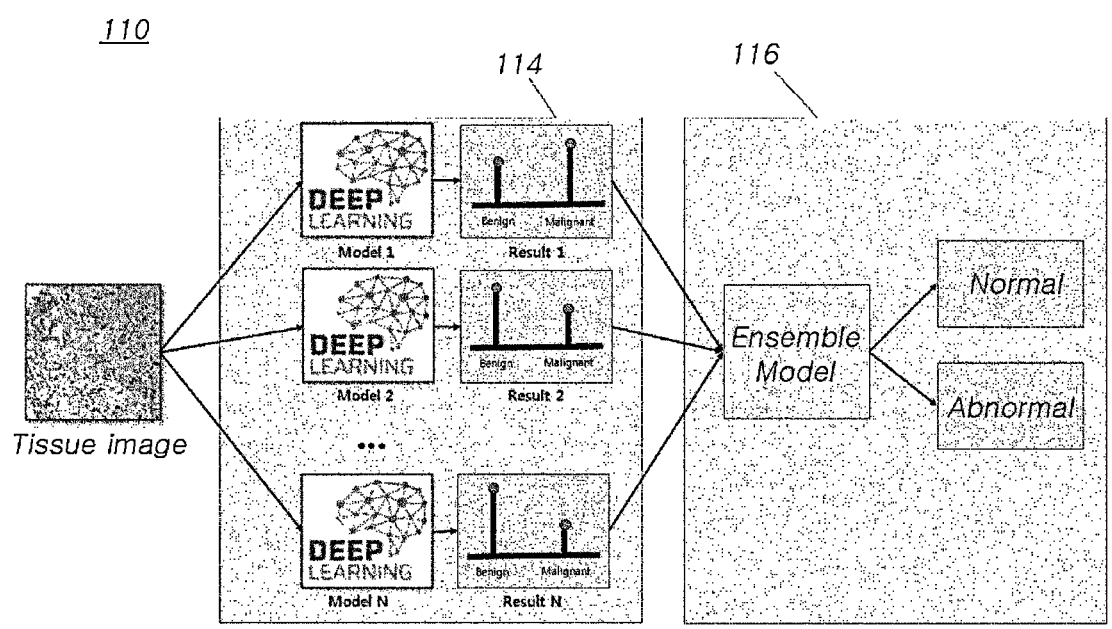
FIG. 5 is a conceptual diagram of an image diagnosis apparatus using a deep learning model, according to another embodiment of the present disclosure.

FIG. 5 is a conceptual diagram of an image diagnosis apparatus using a deep learning model, according to another embodiment of the present disclosure.

Referring to FIG. 5, an image diagnosis apparatus 110 using a deep learning model, according to another embodiment of the present disclosure, includes an image input part (not illustrated) receiving an image, a classifier 114 classifying the image with two or more trained deep learning models using a weighted loss function to which different weights are assigned, and a result output part 116 combining results of classification by the two or more deep learning models (DEEP LEARNING Models 1 to N, where N is a natural number greater than 2) in the classifier 114 and outputs a final result.

The image input part (not illustrated) may be the same as the image input part 12 described with reference to FIGS. 1 and 2.

The classifier 114 classifies the image with two or more learned deep learning models and outputs a result of classification by the two or more deep learning models. The classifier 114 may be understood as including two or more classifiers 14 respectively including the feature extraction part 142 and the classification part 144 described with reference to FIG. 3, or including two or more deep learning models respectively including the feature extraction part 142 and the classification part 144.

All or part of the deep learning models may apply the dropout technique described above with reference to FIGS. 4A and 4B.

The two or more deep learning models may be different deep learning models. Therefore, the different deep learning models may exhibit different sensitivities or specificities even if images are classified using the same weighted loss function.

For example, at least part of the deep learning models may be a deep learning model using the same single deep learning model, but trained by adjusting the number or order of pieces of training data used for training one deep learning model.

As another example, at least part of the deep learning models may be a deep learning model using the same single deep learning model, but applying different dropout techniques.

In the present embodiment, deep learning models may be created by applying random sampling (data order random) and dropout techniques.

As another example, at least part of the deep learning models may be deep learning models having different layer depths or a different number of layers. For example, one deep learning model may have 35 layer depths or 35 layers, and another deep learning model may have 35 layer depths or 35 layers.

As described above, if one structurally identical deep learning model is used to create two or more different deep learning models or to create structurally different deep learning models, two or more deep learning models may include a combination thereof.

The result output part 116 ensembles classification results of the two or more deep learning models, classifies the tissue included in the medical image as being one of normal and abnormal in terms of the presence of disease, and outputs a final result.

As described above, since the deep learning models are different from each other, the deep learning models may exhibit different sensitivities or specificities. Therefore, the sensitivity or the specificity may be further increased by ensembling the classification results of the deep learning models.

The result output part 116 may ensemble the classification results of the two or more deep learning models based on at least one of a majority vote-based ensemble, a unanimity-based ensemble, or an uncertainty-based ensemble, classify the tissue included in the medical image as being one of normal and abnormal in terms of the presence of disease, and output a final classification result.

The deep learning models use highly flexible nonlinear algorithms. Therefore, the result values of the deep learning models may exhibit a large deviation. It is possible to reduce the deviation of the classification results, that is, the result values of the deep learning models that ensemble the classification results of the deep learning models based on at least one of the majority vote-based ensemble, the unanimity-based ensemble, or the uncertainty-based ensemble.

In other words, the deep learning models learn different internal parameters according to a learning method, for example, sampling order and randomness of dropout. Even if the training is performed using the same data and the same deep learning models, different results may be obtained for each deep learning model. Therefore, using the single deep learning model may involve a risk of a determination error. Therefore, in the present embodiment, it is possible to create the various deep learning models and minimize a risk of a determination error through the ensemble technique.

The result output part 116 may apply the majority vote-based ensemble, the unanimity-based ensemble, and the uncertainty-based ensemble as an ensemble model that ensembles the classification results of two or more deep learning models.

In the ensemble model, the majority vote-based ensemble determines the final classification result by a majority vote among the classification results of two or more deep learning models. For example, in a case in which the number of deep learning models is 5, if the classification results of three deep learning models are normal and the classification results of two deep learning models are abnormal, the result output part 116 may output a final classification result as normal, which is a majority of classification results.

The number of deep learning models used to ensemble the classification results of the deep learning models is not limited to two or more, but may be an odd number so as to determine the final classification result by majority vote.

In the ensemble model, the unanimity-based ensemble outputs the unanimous classification result as the final classification result.

For example, if the classification results of the five deep learning models in the above example are all normal, the output part 116 may output a final classification result as normal, which is a majority of classification results. As another example, if the classification results of the five deep learning models in the above example are all abnormal, the output part 116 may output a final classification result as abnormal, which is a majority of classification results.

As described above, the classification results of the three deep learning models may be normal and the classification results of the two deep learning models may be abnormal. As a result of applying the unanimity-based ensemble as the ensemble model, the output part 116 may ultimately determine the classification result by reflecting the relative magnitudes of the weights of the weighted loss function.

For example, in the weighted loss function, if the second weight $W_2$ is greater than the first weight $W_1$, it may be more dangerous to determine the feature as being normal even though the feature is abnormal. If even one deep learning model determines the feature as being abnormal, the result output part 116 may ultimately determine the classification result as being abnormal.

On the contrary, in the weighted loss function, if the first weight $W_1$ is greater than the second weight $W_2$, it may be more dangerous to determine the feature as being abnormal even though the feature is normal. If even one model determines the feature as being normal, the result output part 116 may ultimately determine the classification result as normal.

As the ensemble model, the uncertainty-based ensemble determines the final classification result through statistical values of classification results of two or more deep learning models.

Uncertainty in the field of deep learning means that, if the deep learning model is not perfect or data is incomplete, the results be should presented probabilistically in consideration of various problems that may occur in training the deep learning model.

As described above, in the initial stage of creating the deep learning model, the tests are performed several times by randomly removing nodes with the dropout technique, and the uncertainty may be estimated probabilistically through the statistical values of the results obtained through the tests.

However, when a test is performed once, for example, because the probability is estimated using the statistical values of the results through 100 or more tests, such a method has a disadvantage in that energy consumption may be high. That is, since such a process is also applied to the learning process of the deep learning model, it may take a very long time to learn.

Therefore, instead of producing various result values by applying the dropout technique to one deep learning model, a plurality of deep learning models are created using random sampling and dropout techniques from the beginning, and the uncertainty or uncertainty value may be obtained from the statistical values thereof (classification results summed by ensemble).

In the present embodiment, two or more deep learning models may be created through random sampling and dropout, and the uncertainty value may be represented by ensembling the results of the two or more deep learning models, that is, the classification results of the two or more deep learning models.

The uncertainty-based ensemble may ensemble the classification results of the two or more deep learning models using either a confidence average or a standard deviation.

The confidence average $\Theta$ is not an uncertainty value, but a simple ensemble value, and the standard deviation $\sigma$ is one of the indicators representing uncertainty.

As the confidence average $\Theta$ or the standard deviation $\sigma$ is smaller, the sensitivity of the final classification result may be increased or the specificity may be lowered. In this regard, in Experimental Examples 4 and 5, it is experimentally proven that, if $W_1:W_2=1:50$ is applied to the weighted loss function of Equation 7, as the confidence average $\Theta$ or the standard deviation $\sigma$ is smaller, the sensitivity of the final classification result may be increased.

The image diagnosis apparatuses 10 and 110 using the deep learning model, according to the embodiments of the present disclosure, have been described above with reference to FIGS. 1 to 5. Hereinafter, an image diagnosis method using a deep learning model, according to another embodiment of Referring to disclosure, will be described with reference to FIG. 6.

Figure 6:
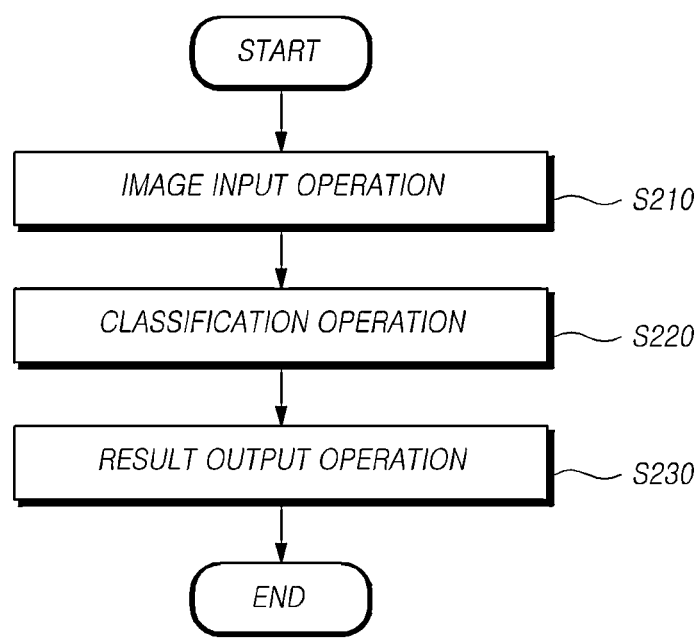
FIG. 6 is a flowchart of an image diagnosis method using a deep learning model, according to another embodiment of the present disclosure.

FIG. 6 is a flowchart of an image diagnosis method using a deep learning model, according to another embodiment of the present disclosure.

Referring to FIG. 6, an image diagnosis method 200 using a deep learning model, according to another embodiment, includes: an image input operation S210 of receiving a medical image including tissue of a human body; a classification operation S220 of classifying the tissue included in the input medical image as being one of normal and abnormal in terms of the presence of disease using a trained deep learning model using a weighted loss function in which different weights are assigned to a probability distribution of determining that a feature extracted from the input medical image is abnormal even though the feature is normal and a probability distribution of determining that the feature is normal even though the feature is abnormal; and a result output operation S230 of outputting a result of classification in the classification operation S220.

As described above with reference to FIG. 3, the deep learning model may include a feature extraction part extracting a feature of the medical image by performing convolution and subsampling on the input medical image, and a classification part performing classification of the input medical image using the weighted loss function for the extracted feature.

As described with reference to Equations 4 to 7, in the weighted loss function, the second weight assigned to the probability distribution of determining that the feature is normal even though the feature is abnormal may be greater than the first weight assigned to the probability distribution of determining that the feature is abnormal even though the feature is normal.

As described above with reference to FIG. 5, the number of deep learning models may be two or more. In the result output operation S230, classification results of the two or more deep learning models may be ensembled, the tissue included in the medical image may be classified as being one of normal and abnormal in terms of the presence of disease, and a classification result may be output.

In the image diagnosis apparatus 110 using the deep learning model as described above with reference to FIG. 5, all or part of the deep learning models may apply a dropout technique that learns training data by removing a node present in each layer with a specific probability p and, when the learning is completed and the test is conducted, considers all nodes as they are and multiplies the probability p by the weight of each node.

At least part of the deep learning models uses the same single deep learning model, but may be trained by adjusting the number or order of pieces of training data used for training one deep learning model.

At least part of the deep learning models may be different from deep learning models having different layer depths or a different number of layers.

In the result output operation S230, the classification results of the two or more learning models may be ensembled based on at least one of a majority vote-based ensemble, a unanimity-based ensemble, or an uncertainty-based ensemble, the tissue included in the medical image may be determined as being one of normal and abnormal in terms of the presence of disease, and a final classification result may be output.

The uncertainty-based ensemble may ensemble the classification results of the two or more deep learning models using either a confidence average or a standard deviation.

The medical image may be the tissue of the human body, for example, liver, stomach, heart, small intestine, large intestine, etc. In addition, a disease may be cancer, inflammation, a rupture, etc. For example, the medical image may be an image captured from the large intestine of the human body, and the disease may be colon cancer.

As described above, a general deep learning model focuses only on increasing the accuracy of image diagnosis when classifying whether or not there is a disease in a corresponding tissue for image diagnosis. On the other hand, since the image diagnosis apparatus using the deep learning model and the method therefor, according to the embodiments of the present disclosure, use the weighted loss function-based deep learning model to which different weights are assigned, it is possible to increase the specificity of image diagnosis or increase the sensitivity of image diagnosis.

Since the image diagnosis apparatus using the deep learning model and the method therefor, according to the embodiments of the present disclosure, use the weighted loss function-based deep learning model to which different weights are assigned, there is an effect of minimizing the false-negative type II error which may result in fatal complications for the patient through an optimal treatment time of a disease being delayed or missed.

Since the image diagnosis apparatus using the deep learning model and the method therefor, according to the embodiments of the present disclosure, ensemble the classification results of two or more deep learning models, it is possible to further increase the specificity of image diagnosis or to further increase the sensitivity of image diagnosis.

Hereinafter, through experimental examples to which the image diagnosis apparatus using the deep learning model and the method therefor, according to the embodiments of the present disclosure, are applied, it can be shown that the sensitivity of image diagnosis may be further increased by minimizing the false-negative type II error which may result in fatal complications for the patient through an optimal treatment time of a disease being delayed or missed.

Experimental Example 1

An individual deep learning model used DenseNet 35 by utilizing residual networks. The dropout technique applied a probability of p=0.5 to a classification layer or a classification part (144 in FIG. 3).

TABLE 2

|  | Output Size | DenseNet35 |
| --- | --- | --- |
| Convolution | 128 × 128 | 7 × 7 conv, stride 2 |
| Pooling | 64 × 64 | 3 × 3 max pool, stride 2 |
| Dense Block (1) | 64 × 64 | [1 × 1 conv, 3 × 3 conv] × 2 |
| Transition Layer (1) | 64 × 64 | 1 × 1 conv |
|  | 32 × 32 | 2 × 2 average pool, stride 2 |
| Dense Block (2) | 32 × 32 | [1 × 1 conv, 3 × 3 conv] × 3 |
| Transition Layer (2) | 32 × 32 | 1 × 1 conv |
|  | 16 × 16 | 2 × 2 average pool, stride 2 |
| Dense Block (3) | 16 × 16 | [1 × 1 conv, 3 × 3 conv] × 5 |
| Transition Layer (3) | 16 × 16 | 1 × 1 conv |
|  | 8 × 8 | 2 × 2 average pool, stride 2 |
| Dense Block (4) | 8 × 8 | [1 × 1 conv, 3 × 3 conv] × 3 |
| Transition Layer (4) | 8 × 8 | 1 × 1 conv |
|  | 4 × 4 | 2 × 2 average pool, stride 2 |
| Dense Block (5) | 4 × 4 | [1 × 1 conv, 3 × 3 conv] × 2 |
| classification Layer | 4 × 4 | 4 × 4 global average pool |
|  | 1 × 1 | 2 D fully-connected |

DenseNet (Densely Connected Convolutional Networks) used in Experimental Example 1 is one of the CNN models published by Gao Huang et al. in a paper (https://arxiv.org/abs/1608.06993) in 2016. DenseNet proposed dense connectivity that continuously adds input values in the channel direction of output values. In Table 2, a transition layer collectively refers to a convolution layer and a subsampling layer. If passing through the transition layer, the size of the feature map is reduced. In order to apply dense connectivity in DenseNet, the sizes of the feature maps may be equal to each other. A dense block is constituted by gathering operations of sharing the same sizes of the feature maps, and dense connectivity is applied therein.

If the number of feature maps that have passed through all the dense blocks is m, the number of feature maps is θm (0<θ≤1) if passing through the transition layer. The value of θ is a designated hyper parameter. If 1, the number of feature maps does not change and continues to accumulate.

As shown in Table 3, in the weighted loss function of Equation 7, an individual deep learning model was created while adjusting the value of the second weight $W_2$ in a state in which the value of the first weight $W_1$ was fixed (operation 1 test of framework).

TABLE 3

| Weight | $W_1$ | $W_2$ |
|---|---|---|
| 1 | 1 | 1 |
| 2 | 1 | 2 |
| 3 | 1 | 3 |
| 4 | 1 | 4 |
| 5 | 1 | 5 |
| 6 | 1 | 10 |
| 7 | 1 | 15 |
| 8 | 1 | 20 |
| 9 | 1 | 25 |
| 10 | 1 | 30 |
| 11 | 1 | 35 |
| 12 | 1 | 40 |
| 13 | 1 | 45 |
| 14 | 1 | 50 |
| 15 | 1 | 55 |
| 16 | 1 | 60 |
| 17 | 1 | 65 |
| 18 | 1 | 70 |
| 19 | 1 | 75 |
| 20 | 1 | 80 |
| 21 | 1 | 85 |
| 22 | 1 | 90 |
| 23 | 1 | 95 |
| 24 | 1 | 100 |

First, the value of the second weight $W_2$ was adjusted to 2 to 100 in Table 3, and other deep learning models were created using training data in Table 4 (operation 2 test of framework).

TABLE 4

|  | NORMAL | ABNORMAL |
|---|---|---|
| Train | 3536 | 3575 |
| Validation | 401 | 401 |
| Test | 340 | 340 |

The results of testing the created deep learning models are shown in Table 5 below.

TABLE 5

| Densent35 | Sensitivity | Specificity | Accuracy |
|---|---|---|---|
| Weight 1:1 ($W_1$:$W_2$) | 98.53 | 99.41 | 98.97 |
| Weight 1:2 | 98.53 | 99.12 | 98.82 |
| Weight 1:3 | 98.82 | 98.82 | 98.82 |
| Weight 1:4 | 98.82 | 98.82 | 98.82 |
| Weight 1:5 | 98.82 | 98.24 | 98.53 |
| Weight 1:10 | 99.41 | 98.24 | 98.82 |
| Weight 1:15 | 99.41 | 97.65 | 98.53 |
| Weight 1:20 | 98.82 | 96.18 | 97.50 |
| Weight 1:25 | 99.12 | 97.94 | 98.53 |
| Weight 1:30 | 99.41 | 95.29 | 97.35 |

TABLE 5-continued

| Densent35 | Sensitivity | Specificity | Accuracy |
|---|---|---|---|
| Weight 1:35 | 99.12 | 96.47 | 97.79 |
| Weight 1:40 | 99.41 | 96.76 | 98.09 |
| Weight 1:45 | 99.71 | 87.35 | 93.53 |
| Weight 1:50 | 99.71 | 95.00 | 97.35 |
| Weight 1:55 | 99.12 | 94.12 | 96.62 |
| Weight 1:60 | 99.41 | 98.24 | 98.82 |
| Weight 1:65 | 99.41 | 90.29 | 94.85 |
| Weight 1:70 | 99.12 | 95.88 | 97.50 |
| Weight 1:75 | 99.41 | 90.29 | 94.85 |
| Weight 1:80 | 100.00 | 65.88 | 82.94 |
| Weight 1:85 | 99.12 | 93.53 | 96.32 |
| Weight 1:90 | 99.41 | 97.35 | 98.38 |
| Weight 1:95 | 99.71 | 88.53 | 94.12 |
| Weight 1:100 | 99.41 | 89.12 | 94.26 |

Figure 7:
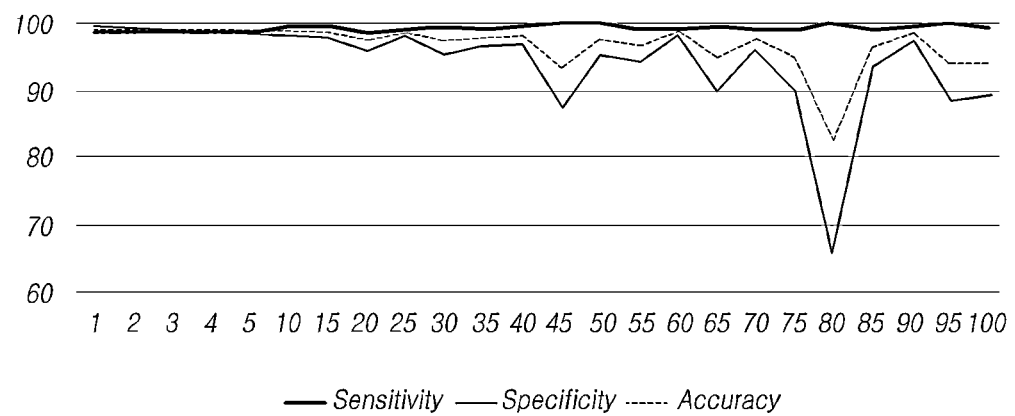
FIGS. 7 and 8 are diagrams illustrating relative sensitivity, specificity, and accuracy according to Experimental Example 3.
Figure 8:
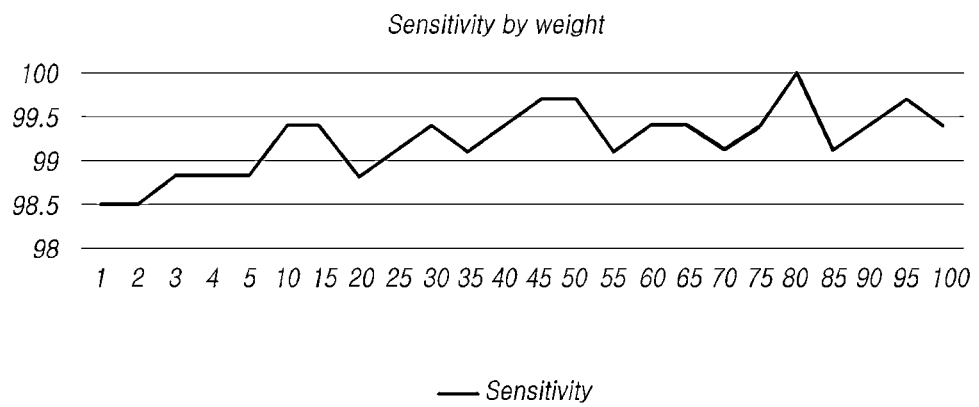

FIGS. 7 and 8 are relative graphs of the sensitivity, the specificity, and the accuracy in Table 5.

Referring to FIG. 7, as a result of classification obtained by testing other deep learning models in which the value of the second weight $W_2$ is adjusted in a state in which the value of the first weight $W_1$ is fixed, it may be confirmed that, in the weighted loss function of Equation 7, as the value of the second weight value $W_2$ increases, the sensitivity is relatively further improved than the specificity and the accuracy.

Referring to FIG. 8, as a result of classification obtained by testing other deep learning models in which the value of the second weight $W_2$ is adjusted in a state in which the value of the first weight $W_1$ is fixed, it may be confirmed that, in the weighted loss function of Equation 7, as the value of the second weight value $W_2$ increases, the sensitivity is also relatively improved, compared with the case in which the value of the second weight $W_2$ is small.

Experimental Example 2

An individual deep learning model used DenseNet 35 (see Table 2) by utilizing residual networks. The dropout technique applied a probability of p=0.5 to a classification layer or a classification part (144 in FIG. 3).

As shown in Table 3, in the weighted loss function of Equation 7, an individual deep learning model was created while adjusting the value of the first weight $W_1$ in a state in which the value of the second weight $W_2$ was fixed (operation 1 test of framework).

First, the value of the second weight $W_2$ was fixed at 50, and five different deep learning models were created by applying random sampling and dropout techniques using the training data in Table 4 (operation 2 test of framework).

The results of testing the created five deep learning models are shown in Table 6 below. In Table 6, DenseNet35 is the result of testing five different deep learning models when $W_1$:$W_2$=1:1, that is, the general loss function is applied in the weighted loss function, and DenseNet35 weight is the result of testing five different deep learning models when $W_1$:$W_2$=1:50 is applied in the weighted loss function of Equation 7.

TABLE 6

| | DenseNet35 (Sampling, Dropout = _5 in FC layer) | | | DenseNet35_weight (Sampling, Dropout = _5 in FC layer) | | |
|---|---|---|---|---|---|---|
| | Sensitivity | Specificity | Accuracy | Sensitivity | Specificity | Accuracy |
| Model_1 | 98.52 | 99.41 | 98.97 | 99.71 | 97.65 | 98.68 |
| Model_2 | 97.94 | 98.52 | 98.24 | 99.41 | 94.12 | 96.76 |
| Model_3 | 98.24 | 99.12 | 98.68 | 99.12 | 92.35 | 95.74 |
| Model_4 | 98.24 | 98.24 | 98.24 | 99.71 | 94.12 | 96.91 |
| Model_5 | 98.82 | 99.70 | 99.26 | 100 | 97.94 | 98.97 |

In Table 6, as a result of classification obtained by testing five different deep learning models, it may be confirmed that, when $W_1:W_2=1:50$ is applied in the weighted loss function of Equation 7, the sensitivity is improved, compared with the specificity and the accuracy.

Experimental Example 3

An individual deep learning model used DenseNet 65 by utilizing residual networks. The dropout technique applied a probability of p=0.5 to a classification layer or a classification part (144 in FIG. 3). DenseNet 65 is basically the same as DenseNet 35 in Experimental Example 1, except that the depth of the layer, that is, the number of layers is 65.

As shown in Table 3, in the weighted loss function of Equation 7, an individual deep learning model was created while adjusting the value of the first weight $W_1$ in a state in which the value of the second weight $W_2$ was fixed (operation 1 test of framework).

First, the value of the second weight $W_2$ was fixed at 50, and five different deep learning models were created by applying random sampling and dropout techniques using the training data in Table 4 (operation 2 test of framework).

The results of testing the created five deep learning models are shown in Table 7 below. In Table 7, DenseNet65 is the result of testing five different deep learning models when $W_1:W_2=1:1$, that is, the general loss function is applied in the weighted loss function, and DenseNet65 weight is the result of testing five different deep learning models when $W_1:W_2=1:50$ is applied in the weighted loss function.

TABLE 7

| | DenseNet65 (Sampling, Dropout = _5 in FC layer) | | | DenseNet65_weight (Sampling, Dropout = _5 in FC layer) | | |
|---|---|---|---|---|---|---|
| | Sensitivity | Specificity | Accuracy | Sensitivity | Specificity | Accuracy |
| Model_1 | 99.41 | 99.12 | 99.26 | 99.71 | 95.00 | 97.35 |
| Model_2 | 99.41 | 99.70 | 99.56 | 99.71 | 96.76 | 98.24 |
| Model_3 | 98.52 | 99.12 | 98.82 | 100 | 90.29 | 95.15 |
| Model_4 | 99.12 | 99.41 | 99.26 | 100 | 95.88 | 97.94 |
| Model_5 | 98.82 | 98.82 | 98.82 | 99.41 | 95.29 | 97.35 |

In Table 7, as a result of classification obtained by testing five different deep learning models, it may be confirmed that, when $W_1:W_2=1:50$ is applied in the weighted loss function, the sensitivity is improved, compared with the specificity and the accuracy.

Experimental Example 4

The classification results of the five deep learning models created in Experimental Examples 1 and 2 were ensembled, and the tissue included in the medical image was classified as being one of normal and abnormal in terms of the presence of disease.

The classification results of the five deep learning models were ensembled based on at least one of a majority vote-based ensemble, a unanimity-based ensemble, or an uncertainty-based ensemble, and the tissue included in the medical image was classified as being one of normal and abnormal in terms of the presence of disease.

In Experimental Example 4, the classification results of the five deep learning models were ensembled using a confidence average for uncertainty-based ensemble (see Tables 8A to 8D). Tables 8A to 8D include the classification results of the five deep learning models in Experimental Examples 1 and 2 and the classification results obtained by ensembling them.

TABLE 8

| | | DenseNet35 (Sampling, Dropout = _5 in FC layer) | | | DenseNet35_weight (Sampling, Dropout = _5 in FC layer) | | | DenseNet65 (Sampling, Dropout = _5 in FC layer) | | | DenseNet65_weight (Sampling, Dropout = _5 in FC layer) | | |
|---|---|---|---|---|---|---|---|---|---|---|---|---|---|
| | | Sensitivity | Specificity | Accuracy | Sensitivity | Specificity | Accuracy | Sensitivity | Specificity | Accuracy | Sensitivity | Specificity | Accuracy |
| individual model | Model_1 | 98.52 | 99.41 | 98.97 | 99.71 | 97.65 | 98.68 | 99.41 | 99.12 | 99.26 | 99.71 | 95 | 97.35 |
| | Model_2 | 97.94 | 98.52 | 98.24 | 99.41 | 94.12 | 96.76 | 99.41 | 99.7 | 99.56 | 99.71 | 96.76 | 98.24 |
| | Model_3 | 98.24 | 89.32 | 98.68 | 99.12 | 92.35 | 95.74 | 98.52 | 99.12 | 98.82 | 100 | 90.29 | 95.15 |
| | Model_4 | 98.24 | 95.24 | 98.24 | 99.71 | 94.12 | 96.91 | 99.12 | 99.41 | 99.26 | 100 | 95.88 | 97.94 |
| | Model_5 | 98.82 | 99.70 | 99.24 | 100 | 97.94 | 98.97 | 98.82 | 98.82 | 98.82 | 99.41 | 95.29 | 97.35 |
| majority vote-based ensemble | | 98.53 | 99.41 | 98.97 | 99.7 | 96.76 | 98.23 | 99.41 | 99.41 | 99.41 | 100 | 96.47 | 98.23 |
| unanimity-based ensemble | | 99.12 | 97.05 | 98.09 | 100 | 88.82 | 94.41 | 99.41 | 98.23 | 98.82 | 100 | 86.76 | 93.38 |
| uncertainty-based ensemble (Θ = average confidence score) | Θ = 5 | 98.52 | 99.12 | 98.82 | 99.71 | 96.76 | 98.24 | 99.41 | 99.41 | 99.41 | 99.71 | 96.47 | 98.09 |
| | Θ = 4 | 98.53 | 99.12 | 98.82 | 99.71 | 95.59 | 97.65 | 99.41 | 99.41 | 99.41 | 100 | 95.29 | 97.65 |
| | Θ = 3 | 98.82 | 98.82 | 98.82 | 100 | 97.94 | 96.47 | 99.41 | 99.11 | 99.26 | 100 | 92.65 | 96.37 |
| | Θ = 2 | 99.12 | 98.53 | 98.82 | 100 | 90.88 | 95.44 | 99.41 | 98.52 | 98.97 | 100 | 87.35 | 93.68 |
| | Θ = 1 | 99.41 | 96.76 | 98.09 | 100 | 85.59 | 92.79 | 99.41 | 97.64 | 98.52 | 100 | 81.76 | 90.88 |
| | Θ = .05 | 99.7 | 95.29 | 97.5 | 100 | 80.59 | 90.29 | 99.41 | 95.58 | 97.5 | 100 | 73.53 | 86.76 |
| | Θ = .01 | 100 | 92.64 | 96.32 | 100 | 66.47 | 83.24 | 99.71 | 92.05 | 95.88 | 100 | 54.71 | 77.35 |

When performed on the image diagnosis apparatus using the actual deep learning model, a value reaching 100% sensitivity for the first time may be found and designated to the confidence average Θ. For example, in Tables 8B and 8D, in the case of the confidence average Θ=0.3 for DenseNet 35_weight and the confidence average Θ=0.4 for DenseNet65_weight, respectively, 100% sensitivity is reached for the first time. Thus, the image diagnosis apparatus using the actual deep learning model may ensemble the classification results of the five deep learning models using the confidence average values.

Experimental Example 5

The classification results of the five deep learning models created in Experimental Examples 1 and 2 were ensembled, and the tissue included in the medical image was classified as being one of normal and abnormal in terms of the presence of disease.

The classification results of the five deep learning models were ensembled based on at least one of a majority vote-based ensemble, a unanimity-based ensemble, or an uncertainty-based ensemble, and the tissue included in the medical image was classified as being one of normal and abnormal in terms of the presence of disease.

In Experimental Example 5, the classification results of the five deep learning models were ensembled using a standard deviation for uncertainty-based ensemble (see Tables 9A to 9D). Tables 9A to 9D include the classification results of the five deep learning models in Experimental Examples 1 and 2 and the classification results obtained by ensembling them.

standard deviation $\sigma$ is smaller, the sensitivity of the final classification result is increased. Specifically, in Experimental Examples 4 and 5, it is experimentally proven that, if $W_1:W_2=1:50$ is applied to the weighted loss function of Equation 7, as the confidence average $\Theta$ or the standard deviation $\sigma$ is smaller, the sensitivity of the final classification result may be increased.

On the other hand, in the case of focusing on increasing the sensitivity of the classification result, the specificity may be relatively lowered, and thus accuracy may be lowered. However, through Experimental Examples 4 and 5, it may confirm that it is possible to increase the sensitivity of the final classification result and to minimize the decrease in specificity and accuracy.

Although the image diagnosis apparatus using the deep learning model and the method therefor, according to the embodiments of the present disclosure, have been described above with reference to the drawings, the present disclosure is not limited thereto.

Figure 9:
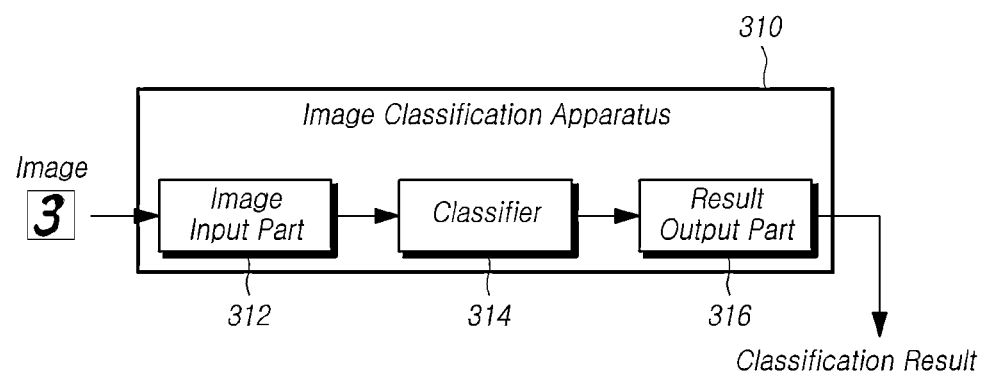
FIG. 9 is a conceptual diagram of an image classification apparatus according to another embodiment of the present disclosure.

For example, the present disclosure may include an image classification apparatus 310 illustrated in FIG. 9 as another embodiment. The image classification apparatus 310 is basically the same as the image diagnosis apparatuses 10 and 110 using the deep learning model described with

TABLE 9

| | | DenseNet35 (Sampling, Dropout = _5 in FC layer) | | | DenseNet35_weight (Sampling, Dropout = _5 in FC layer) | | | DenseNet65 (Sampling, Dropout = _5 in FC layer) | | | DenseNet65_weight (Sampling, Dropout = _5 in FC layer) | | |
|---|---|---|---|---|---|---|---|---|---|---|---|---|---|
| | | Sensi-tivity | Speci-ficity | Accu-racy | Sensi-tivity | Speci-ficity | Accu-racy | Sensi-tivity | Speci-ficity | Accu-racy | Sensi-tivity | Speci-ficity | Accu-racy |
| individual model | Model_1 | 98.52 | 99.41 | 98.97 | 99.71 | 97.65 | 98.68 | 99.41 | 99.12 | 99.26 | 99.71 | 95 | 97.35 |
| | Model_2 | 97.94 | 98.52 | 98.24 | 99.41 | 94.12 | 96.76 | 99.41 | 99.7 | 99.56 | 99.71 | 96.76 | 98.24 |
| | Model_3 | 98.24 | 99.11 | 98.68 | 99.12 | 92.35 | 95.74 | 98.52 | 99.12 | 98.82 | 100 | 90.29 | 95.15 |
| | Model_4 | 98.24 | 98.24 | 98.24 | 99.71 | 94.12 | 96.91 | 99.12 | 99.41 | 99.26 | 100 | 95.88 | 97.94 |
| | Model_5 | 98.82 | 99.7 | 99.26 | 100 | 97.94 | 98.97 | 98.82 | 98.82 | 98.82 | 99.41 | 95.29 | 97.35 |
| majority vote-based ensemble | | 98.53 | 98.97 | 98.97 | 99.7 | 95.76 | 98.23 | 99.41 | 99.41 | 99.41 | 100 | 96.47 | 98.23 |
| unanimity-based ensemble | | 99.12 | 97.05 | 98.09 | 100 | 85.82 | 94.41 | 99.41 | 98.23 | 98.82 | 100 | 86.76 | 93.38 |
| uncertainty-based ensemble ($\sigma$ = standard deviation) | $\sigma$ = 5 | 98.82 | 99.12 | 98.97 | 99.71 | 96.76 | 98.24 | 99.41 | 99.41 | 99.41 | 99.71 | 96.47 | 98.09 |
| | $\sigma$ = 4 | 98.82 | 98.82 | 98.82 | 99.71 | 95.59 | 97.65 | 99.41 | 99.41 | 99.41 | 100 | 95.29 | 97.65 |
| | $\sigma$ = 3 | 99.12 | 97.94 | 95.52 | 100 | 92.94 | 96.47 | 99.41 | 98.82 | 99.11 | 100 | 92.65 | 96.32 |
| | $\sigma$ = 2 | 99.41 | 97.06 | 98.24 | 100 | 90.88 | 95.44 | 99.41 | 98.52 | 98.97 | 100 | 87.35 | 93.68 |
| | $\sigma$ = 1 | 99.70 | 95.29 | 97.5 | 100 | 85.59 | 92.79 | 99.41 | 95.88 | 97.64 | 100 | 81.76 | 90.88 |
| | $\sigma$ = .05 | 99.70 | 94.41 | 97.06 | 100 | 80.59 | 90.29 | 99.71 | 94.71 | 97.21 | 100 | 73.53 | 86.76 |
| | $\sigma$ = .01 | 100 | 92.06 | 96.03 | 100 | 65.47 | 83.24 | 99.71 | 89.12 | 94.41 | 100 | 54.71 | 77.35 |

When performed on the image diagnosis apparatus using the actual deep learning model, a value reaching 100% sensitivity for the first time may be found and designated to the standard deviation $\sigma$. For example, in Table 9, in the case of the standard deviation $\sigma=0.3$ for DenseNet 35_weight and the standard deviation $\sigma=0.4$ for DenseNet65_weight, 100% sensitivity is reached for the first time. Thus, the image diagnosis apparatus using the actual deep learning model may ensemble the classification results of the five deep learning models using the standard deviation.

Through Experimental Examples 4 and 5, the classification results of the five deep learning models are ensembled based on at least one of a majority vote-based ensemble, a unanimity-based ensemble, or an uncertainty-based ensemble, and the tissue included in the medical image is classified as being one of normal and abnormal in terms of the presence of disease. As a result of the classification, it may be confirmed that the sensitivity is further improved.

In addition, through Experimental Examples 4 and 5, it may be confirmed that, as the confidence average $\Theta$ or the reference to FIGS. 1 to 5. However, an input image may be a general image instead of a medical image, and a classification result may be a general image classification instead of detection of the presence or absence of a disease. For example, the input image may be a handwritten number as illustrated in FIG. 9, the classification result may be a number included in the image, and the image classification apparatus 310 may be a number classification apparatus.

The image classification apparatus 310 may include an image input part 312, a classifier 314, and a result output part 316, as in the image diagnosis apparatuses 10 and 110 using the deep learning model. These configurations may be substantially the same as the image input parts 12, the classifiers 14 and 114, and the result output parts 16 and 116 of the image diagnosis apparatuses 10 and 110 using the deep learning model.

The image diagnosis apparatuses 10 and 110 using the deep learning model and the image classification apparatus 310 may be implemented by a computing device including at least one of a processor, a memory, a user input device, or a presentation device. The memory is a medium that stores computer-readable software, applications, program modules, routines, instructions, and/or data, which are coded to perform specific tasks when executed by the processor. The processor may read and execute the computer-readable software, applications, program modules, routines, instructions, and/or data, which are stored in the memory. The user input device may be a means for allowing the user to input a command to the processor to execute a specific task or to input data required for the execution of the specific task. The user input device may include a physical or virtual keyboard or keypad, a key button, a mouse, a joystick, a trackball, a touch-sensitive input means, or a microphone. The presentation device may include a display, a printer, a speaker, or a haptic device.

The computing device may include various devices such as smartphones, tablets, laptops, desktops, servers, clients, and the like. The computing device may be a single stand-alone device, and may include a plurality of computing devices operating in a distributed environment including a plurality of computing devices cooperating with each other through a communication network.

In addition, the image diagnostic method described above may be executed by a computing device including a processor and a memory storing computer-readable software, applications, program modules, routines, instructions, and/or data structures, which are coded to perform the image diagnosis method using the deep learning model when executed by the processor.

The above-described embodiments may be implemented through various means. For example, the present embodiments may be implemented by hardware, firmware, software, or a combination thereof.

When implemented by hardware, the image diagnosis method using the deep learning model, according to the present embodiments, may be implemented by one or more application specific integrated circuits (ASICs), digital signal processors (DSPs), digital signal processing devices (DSPDs), programmable logic devices (PLDs), field programmable gate arrays (FPGAS), processors, controllers, microcontrollers, or microprocessors.

For example, the image diagnosis method using the deep learning model, according to the embodiments, may be implemented using an artificial intelligence semiconductor device in which neurons and synapses of a deep neural network are implemented as semiconductor elements. In this case, the semiconductor elements may be currently used semiconductor devices, for example, SRAM, DRAM, NAND, or the like, may be next-generation semiconductor elements, for example, RRAM, STT MRAM, PRAM, or the like, or may be a combination thereof.

When the image diagnosis method using the deep learning model, according to the embodiments, is implemented using an artificial intelligence semiconductor device, the results (weights) of learning the deep learning model through software may be transcribed into synaptic elements arranged in an array, or learning may be carried out in an artificial intelligence semiconductor device.

When implemented by firmware or software, the image diagnosis method using the deep learning model, according to the present embodiments, may be implemented in the form of an apparatus, procedure, or function performing the functions or operations described above. The software code may be stored in a memory unit and driven by a processor. The memory unit may be disposed inside or outside the processor, and may exchange data with the processor by various well-known means.

In addition, the terms "system", "processor", "controller", "component", "module", "interface", "model", or "unit" as used herein generally refer to computer-related entities hardware, a combination of hardware and software, software, or running software. For example, the above-described components may be a process to be driven by a processor, a processor, a controller, a control processor, an object, a thread of execution, a program, and/or a computer, but is not limited thereto. For example, both the application, which is running on the controller or the processor, and the controller or the processor may be the components. One or more components may reside within a process and/or a thread of execution, and the components may be located on one device (e.g., a system, a computing device, etc.) or may be located on two or more devices in a distributed manner.

The above description and the accompanying drawings provide an example of the technical idea of the present disclosure for illustrative purposes only. Those having ordinary knowledge in the technical field, to which the present disclosure pertains, will appreciate that various modifications and changes in form, such as combination, separation, substitution, and change of a configuration, are possible without departing from the essential features of the present disclosure. The embodiments disclosed in the present disclosure are intended to illustrate the scope of the technical idea of the present disclosure, and thus the scope of the present disclosure is not limited by the embodiments. The scope of the present disclosure shall be construed on the basis of the accompanying claims in such a manner that all of the technical ideas included within the scope equivalent to the claims belong to the present disclosure.

The invention claimed is:

1. An image diagnosis apparatus using a deep learning model, comprising:
   an image input part receiving a medical image including tissue of a human body;
   a classifier classifying the tissue included in the medical image as being one of normal and abnormal in terms of the presence of disease using a trained deep learning model using a weighted loss function in which different weights are assigned to a probability distribution of determining that a feature extracted from the input medical image is abnormal even though the feature is normal and a probability distribution of determining that the feature is normal even though the feature is abnormal; and
   a result output part outputting a result of classification by the classifier.

2. The image diagnosis apparatus of claim 1, wherein the deep model learning includes a feature extraction part extracting the feature of the medical image by performing convolution and subsampling on the input medical image, and a classification part classifying the input medical image using the weighted loss function with respect to the extracted feature.

3. The image diagnosis apparatus of claim 1, wherein, in the weighted loss function, a second weight assigned to the probability distribution of determining that the feature is normal even though the feature is abnormal is greater than a first weight assigned to the probability distribution of determining that the feature is abnormal even though the feature is normal.

4. The image diagnosis apparatus of claim 3, wherein the number of the deep learning model is two or more, and the result output part ensembles classification results of the two or more deep learning models and classifies the tissue included in the medical image as being one of normal and abnormal in terms of the presence of disease.

5. The image diagnosis apparatus of claim 4, wherein all or part of the deep learning models applies a dropout technique that learns training data by removing a node present in each layer with a specific probability and, when the learning is completed and a test is conducted, considers all nodes as they are and multiplies the probability by a weight of each node.

6. The image diagnosis apparatus of claim 4, wherein at least part of the deep learning models use a same single deep learning model and are trained by adjusting a number or order of pieces of training data used for training the single deep learning model.

7. The image diagnosis apparatus of claim 4, wherein at least part of the deep learning models are different from deep learning models having different layer depths or a different number of layers.

8. The image diagnosis apparatus of claim 4, wherein the result output part ensembles classification results of the two or more deep learning models based on at least one of a majority vote-based ensemble, a unanimity-based ensemble, or an uncertainty-based ensemble, and classifies the tissue included in the medical image as being one of normal and abnormal in terms of the presence of disease.

9. The image diagnosis apparatus of claim 8, wherein the uncertainty-based ensemble ensembles the classification results of the two or more deep learning models using either a confidence average or a standard deviation.

10. The image diagnosis apparatus of claim 9, wherein the medical image is an image captured from large intestine of the human body, and the disease is colon cancer.

11. An image diagnosis method using a deep learning model, comprising:
   an image input operation of receiving a medical image including tissue of a human body;
   a classification operation of classifying the tissue included in the input medical image as being one of normal and abnormal in terms of the presence of disease using a trained deep learning model using a weighted loss function in which different weights are assigned to a probability distribution of determining that a feature extracted from the input medical image is abnormal even though the feature is normal and a probability distribution of determining that the feature is normal even though the feature is abnormal; and
   a result output operation of outputting a result of classification in the classification operation.

12. The image diagnosis method of claim 11, wherein the deep learning model includes a feature extraction part configured to extract the feature of the medical image by performing convolution and subsampling on the input medical image, and a classification part configured to classify the input medical image using the weighted loss function with respect to the extracted feature.

13. The image diagnosis apparatus of claim 11, wherein, in the weighted loss function, a second weight assigned to the probability distribution of determining that the feature is normal even though the feature is abnormal is greater than a first weight assigned to the probability distribution of determining that the feature is abnormal even though the feature is normal.

14. The image diagnosis method of claim 13, wherein the number of the deep learning model is two or more, and
   in the result output operation, classification results of the two or more deep learning models are ensembled and the tissue included in the medical image is classified as being one of normal and abnormal in terms of the presence of disease.

15. The image diagnosis method of claim 14, wherein all or part of the deep learning models applies a dropout technique that learns training data by removing a node present in each layer with a specific probability and, when the learning is completed and a test is conducted, considers all nodes as they are and multiplies the probability by a weight of each node.

16. The image diagnosis method of claim 14, wherein at least part of the deep learning models use a same single deep learning model and are trained by adjusting a number or order of pieces of training data used for training the single deep learning model.

17. The image diagnosis method of claim 14, wherein at least part of the deep learning models are different from deep learning models having different layer depths or a different number of layers.

18. The image diagnosis method of claim 14, wherein in the result output operation, the classification results of the two or more deep learning models are ensembled based on at least one of a majority vote-based ensemble, a unanimity-based ensemble, or an uncertainty-based ensemble, and the tissue included in the medical image is classified as being one of normal and abnormal in terms of the presence of disease.

19. The image diagnosis method of claim 18, wherein the uncertainty-based ensemble ensembles the classification results of the two or more deep learning models using either a confidence average or a standard deviation.

20. The image diagnosis method of claim 19, wherein the medical image is an image captured from large intestine of the human body, and the disease is colon cancer.

* * * * *